United States Patent [19]

Butler et al.

[11] 4,286,066

[45] Aug. 25, 1981

[54] CONTINUOUS FERMENTATION AND DISTILLATION APPARATUS

[76] Inventors: Robert S. Butler; Lance B. Crombie, both c/o Crombie-Butler Corp., 1306 W. CO Rd. F., St. Paul, Minn. 55112

[21] Appl. No.: 162,660

[22] Filed: Jun. 24, 1980

[51] Int. Cl.³ .............................................. C12M 1/02
[52] U.S. Cl. .................................... 435/316; 202/205; 203/25; 203/DIG. 1; 203/DIG. 8; 203/DIG. 13
[58] Field of Search ............... 435/316, 302, 161, 162; 127/37, 38; 99/276, 277, 278; 202/173, 205; 203/DIG. 1, DIG. 8, 91, 25, 26, 19; DIG. 13

[56] References Cited

U.S. PATENT DOCUMENTS

| 102,633 | 5/1870 | Wheeler et al. ............... 203/DIG. 1 |
| 2,280,093 | 4/1942 | Kleinschmidt .......................... 203/26 |
| 2,370,665 | 3/1945 | Jeffreys ................................. 435/316 |
| 2,389,064 | 11/1945 | Latham, Jr. ........................... 203/26 |
| 3,834,296 | 9/1974 | Kehse et al. ............................ 99/276 |
| 3,989,848 | 11/1976 | Moll et al. ............................ 435/316 |
| 4,093,516 | 6/1978 | Lang ................................. 203/DIG. 13 |

FOREIGN PATENT DOCUMENTS 2405993 12/1977 France ......................................... 203/19

Primary Examiner—Benoît Castel
Attorney, Agent, or Firm—Dressler, Goldsmith, Shore, Sutker & Milnamow, Ltd.

[57] ABSTRACT

Apparatus for continuously fermenting a moist particulate feed and distilling the fermentation product is disclosed in which a pressure-locked auger forces a moist particulate feed from a hopper into a fermentation tank, liquor is removed from the tank and solids are separated therefrom to produce a beer which is distilled in a distillation column. A combustion engine powers the auger and the means for separating solids, and the engine exhaust surrounds an inlet section of said auger to help heat the pressurized feed therein to produce fermentable sugar within the auger, and the auger includes a section passing to the tank in heat exchange relation to the distillation column to provide heat for distillation. The column is a multistage column angled to face the sun and has an upper glass plate to allow solar radiation to enter and penetrate between the foraminous plates of the column.

7 Claims, 1 Drawing Figure

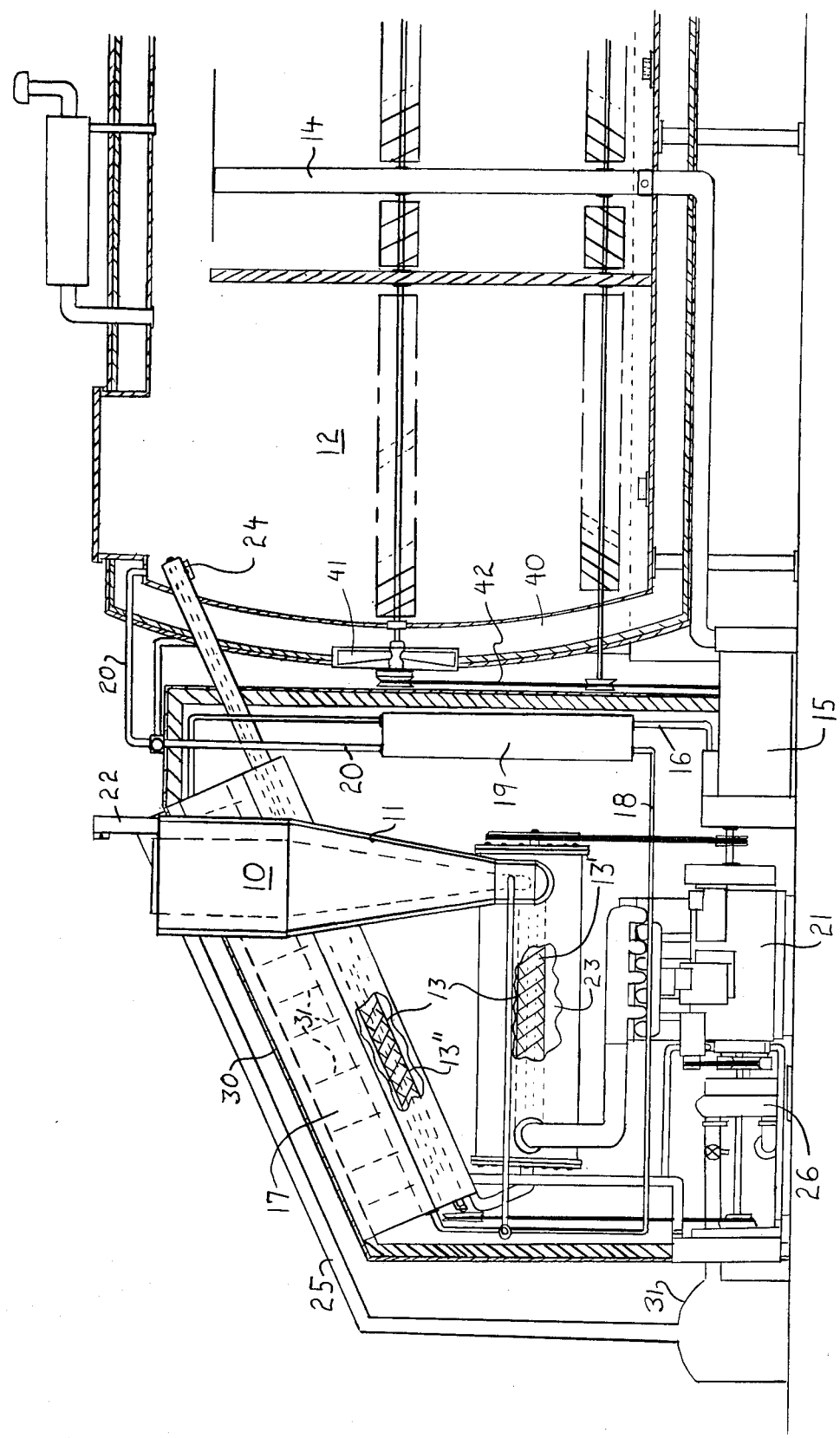

CONTINUOUS FERMENTATION AND DISTILLATION APPARATUS

DESCRIPTION

Technical Field

This invention relates to apparatus for the production of ethyl alcohol, particularly to provide a combustible liquid fuel.

BACKGROUND ART

Fermentation to produce ethyl alcohol is itself well known, but the existing processes require large amounts of heat and are slow and cumbersome such that, even using complex equipment to maximize efficiency, it is questionable as to whether the energy which can be obtained by combustion of the alcohol product will exceed the energy needed to produce and distill the alcohol. In an application filed Feb. 4, 1980 by one of us, Ser. No. 118,433 a simplified process was described in which a moist finely divided feed containing a component convertible to a fermentable sugar is supplied to a fermentation tank under pressure and at high temperature while most of the water or other liquor to be used in the fermentation process is separately supplied. In this way only the moist feed is heated to the point where conversion to fermentable sugar occurs, and the balance of the fermentation liquor, called the wort, does not have to be heated in practice. The wort is withdrawn continuously or periodically and distilled, and a sizable portion of the heat requirement has to be devoted to vaporizing the beer which is produced when the wort is centrifuged to remove solids therefrom.

This invention relates to apparatus for carrying the process of said prior application in an energyefficient manner.

DISCLOSURE OF THE INVENTION

In this invention, apparatus is provided for continuously fermenting a moist particulate feed and for distilling the fermentation product in which a hopper for supplying a moist particulate feed containing a component convertible to fermentable sugar, a fermentation tank, a pressure-locked auger for forcing said feed under pressure from the hopper into the tank, are combined with means to remove the liquor within the tank, a separator, preferably a continuous centrifuge, for separating solids from the removed liquor to produce a beer and a distillation column for distilling the beer which is produced. In this combination, a combustion engine, such as a diesel engine, is employed to power the auger and the separator, and this provides a hot exhaust which surrounds the inlet end of the auger to help heat the feed and cause the production of fermentable sugar within the auger. The contents of the auger are thus heated by the exhaust and by the pressure imposed on the moist feed by the auger, so the auger is at the highest temperature available in the system. This hot auger passes from the exhaust to the tank in heat exchange relation to the distillation column to provide the heat needed for distillation.

As a feature of the invention, the distillation column is positioned at an angle facing the sun and has a glass plate on top so that when solar radiation is available, it can penetrate between the plates of the column to speed the distillation process.

Also, a heat exchanger is employed to preheat the beer supplied to the column and to cool the spent beer, a portion of which is returned to the tank.

In preferred practice, the combustion engine also powers a vacuum pump which reduces the pressure in the distillation column. Also, the hopper is jacketed, and the exhaust leaving the auger passes through this jacket to preheat the moist feed within the hopper.

At least a portion of the spent beer leaving the heat exchanger is returned to the fermentation tank since it still contains unfermented sugar and some residual heat. Fermentation is an exothermic reaction, and even when considerable heat is lost by the tank, the heat supplied to the particulate feed and the heat returned in the spent beer are adequate to maintain the temperature of the wort.

Cooling is only needed in two locations, namely, to condense ethyl alcohol carried away in the carbon dioxide which is produced in the fermentation tank, and to condense ethyl alcohol in the vapors exiting from the top of the ditillation column. Air cooling is normally sufficient for these purposes, but the water supplied to the fermentation tank may also be used, or water not used in the process can be employed and then dumped.

The result is a simple integrated apparatus in which the energy supplied by the combustion engine is very effectively utilized both to power the needed equipment, and to supply heat where needed for conversion to sugar, for fermentation, and for distillation. The capacity to use solar radiation is also helpful toward minimizing the energy requirement so as to obtain a net gain in energy from the production of crops and their fermentation and distillation.

BRIEF DESCRIPTION OF DRAWINGS

The invention is illustrated in a single FIGURE of drawing which is a diagrammatic side elevation, partly in section.

BEST MODE FOR CARRYING OUT THE INVENTION

Referring more particularly to the drawing, a hopper 10 is provided to store a moist particulate feed which may contain a trace of acid to speed the conversion of starch, for example, to fermentable sugar. The hopper 10 is jacketed at 11 so that the feed can be preheated as will be explained.

Fermentation is carried out in a fermentation tank 12, the details of which form no part of this invention. The tank shown includes agitators and similar structure, but these are not unusual and may be omitted. A pressure-locked auger 13 is provided for withdrawing the particulate feed from the bottom of the hopper 11 and for pressurizing and heating the feed as it passes through the auger. The inlet section 13' of the auger is surrounded by an exhaust 23 which assists the heating of the pressurized feed to a temperature at which the starch within the feed will rapidly convert to fermentable sugar. In the presence of a trace of acid, the starch in ground corn will convert in from 7 to 30 seconds to fermentable sugar at a temperature of about 360° F.

Means are provided, such as an overflow line 14 in the tank 12, to continuously remove the wort which, in a continuous process, still contains some sugar which has not been converted to alcohol in the fermentation process. The removed wort passes through line 14 to a continuous centrifugal separator 15 which removes the solids which are suspended in the wort and produces a "beer" which is an aqueous liquor containing alcohol, sugar, and diverse other soluble materials. This beer is pumped via line 16 to a multistage distillation column 17 which is positioned at an angle to face the sun. Column 17 is formed with a glass upper plate 30 and foraminous plates 31 so that the sun can penetrate between the plates.

The beer passes down the column 17 and the alcohol moves up the column so, as is conventional, the liquor at the bottom of the column has the alcohol stripped out of it, and is known as spent beer. At the top of the column is the concentrated alcohol, usually containing from 60% to 95% alcohol, balance water, depending upon the heat input to the column and the rate at which the beer is passed through. The temperature within the column increases as one goes down the column, as is well known in the art of distillation. The spent beer is withdrawn at the bottom of the column via line 18 and the spent beer is passed through a heat exchanger 19 to preheat the incoming beer. This also serves to cool the spent beer which is passed through line 20 and then most of it is returned to the tank 12. Water is also supplied to tank 12 to complete the production of the wort, but this is not shown in the drawing. The balance of the spent beer constitutes product. One use is to combine the spent beer with the dried solids to increase the sugar content of these solids.

The power to operate the system is provided by a combustion engine 21 which is preferably a diesel engine. The exhaust from the engine surrounds the first section 13' of the auger as shown at 23 so that as much heat as possible goes into the moist feed. After heating auger section 13', the exhaust gases pass through jacket 11 to preheat the moist feed in the hopper 10. By this time, the sensible heat in the exhaust is expended, and it is released at 22.

The second stage 13'' of the auger 13 passes along the length of the distillation column 17 as it moves to the tank 12 where it terminates at 24, the hot converted feed dropping into the wort within the tank. The agitation of the tank carries the solid feed into the wort where the soluble portion dissolves and the remaining solids becomes suspended in the aqueous liquor.

As will be evident, the auger section 13'' moves in heat exchange relation to the column 17 and it supplies heat at the elevated temperature needed for distillation. It will be appreciated that much of the heat needed is supplied in the heat exchanger 19 where the incoming beer acquires much of the heat carried away by the exiting spent beer. It will also be appreciated that solar radiation passing through glass pane 30 will penetrate between the plates 31 of column 17 to heat the material within the column when the sun is shining. However, additional heat is sometimes needed for the vaporization of the alcohol and the water contained therein to supply the vapor phase product which is withdrawn from the column 17 via line 25. Line 25 is exposed to the atmosphere which provides most of the cooling needed during most of the year. The alcohol product passes to a collecting tank 31 which is connected to the vacuum line.

Vacuum is provided by a pump 26 which is also powered by the engine 21. The use of vacuum is preferred because it reduces the temperature at which distillation occurs, as is itself well known. however, vacuum need not be used in this invention.

In operation, the fermentation process is continuous with the wort building up and overflowing to exit tank 12 via line 14. The removed wort has its solids removed by the centrifugal separator 15 to provide a valuable solid product useful as animal feed, and it also provides a beer which is passed via line 16 through heat exchanger 19 to the distillation column 17. The spent beer is removed from the bottom of the column and passed to the heat exchanger 19 to preheat the beer and a portion of the cooled spent beer is returned to the tank, the balance being withdrawn as product. Fresh water is added to provide the desired solids content within the wort.

An engine 21 powers the centrifuge 15 and also powers the two section pressure-locked auger 13 which takes preheated moist feed from the hopper 10 and pressurizes it and sends it through the engine exhaust 23 to further heat it. The second stage of the auger then passes through the angled multistage distillation column 17 to supply heat thereto. This allows the process to continue when the sun is not shining and it supplements the solar radiation when it is available. The solid feed containing fermentable sugar is ejected from auger 13 into the fermentation tank to provide the sugar needed to continue the fermentation process.

Various ancillary matters should also be noted.

First, the tank 12 may be double walled, as shown, and the exhaust from engine 21 may be brought into the space 40 between the walls, by means not shown. Cooling of the tank 12 may be achieved, when desired, by fan 41 which taps off the power of engine 21 by means of a belt drive 42. This belt drive 42 may also be used to power agitators 43 if mechanical agitation is desired.

It will also be appreciated that cooling water is run through the engine 21 to prevent overheating thereof, and this provides hot water which may be run through the upper end of the distillation column 17 by means not shown. This provides heat for distillation and cools the water which is returned to the engine.

The engine 21 conventionally includes an alternator or generator which provides an electrical current which may be used to control the various valves which are employed to regulate the flow of fluids and liquids in response to the temperatures which exist in the various portions of the apparatus.

It will therefore be noted that the engine 21 powers everything in one way or another, so there is no boiler or external electrical supply, and this provides a self-contained fermentation and distillation unit which can be placed where ever one wishes.

What is claimed is:

1. Apparatus for continuously fermenting a moist particulate feed and distilling the fermentation product comprising, a hopper for supplying a moist particulate feed containing a component convertible to fermentable sugar, a fermentation tank, pressure-locked auger means for forcing said feed from said hopper into said tank, means to progressively remove liquor from within said tank, means for separating solids from said removed liquor to produce a beer, a distillation column operatively connected to said means for separating solids for distilling said beer, a combustion engine for powering said auger and said means for separating solids, said engine having an exhaust surrounding an inlet section of said auger to help heat said feed and thereby produce fermentable sugar within said auger, and said auger including a section passing from said exhaust to said tank in heat exchange relation to said distillation column to provide heat for distillation.

2. Apparatus as recited in claim 1 further comprising a heat exchanger operatively connected to preheat the beer supplied to said column and to cool spent beer removed from said column, and means to return a portion of said spent beer to said tank.

3. Apparatus as recited in claim 1 in which said engine also powers a vacuum pump which reduces the pressure in the distillation column.

4. Apparatus as recited in claim 1 in which said hopper is jacketed, and the exhaust leaving the auger passes through said jacket to preheat said moist feed.

5. Apparatus as recited in claim 1 in which said means for separating solids is a continuous centrifuge.

6. Apparatus as recited in claim 1 in which said distillation column is a multistage column angled to face the sun and having an upper glass plate to allow solar radiation to enter the column, said column having foraminous plates positioned to be penetrated by the solar radiation.

7. Apparatus as recited in claim 1 in which said fermentation tank is jacketed and fan means are provided to blow cooling air through the jacket to cool the tank.

* * * * *